United States Patent [19]

Koga et al.

[11] 4,295,047
[45] Oct. 13, 1981

[54] EMISSION COMPUTED TOMOGRAPH

[75] Inventors: Kenichiro Koga; Yoshiharu Hirose, both of Kyoto; Iwao Kanno, Akita; Kazuo Uemura, Akita; Shuichi Miura, Akita, all of Japan

[73] Assignee: Shimadzu Corporation, Japan

[21] Appl. No.: 112,787

[22] Filed: Jan. 16, 1980

[30] Foreign Application Priority Data

Jan. 23, 1979 [JP] Japan .................... 54-7390

[51] Int. Cl.$^3$ .......................... G01T 1/20; G21K 1/04
[52] U.S. Cl. ................................ 250/363 S; 250/505; 250/511
[58] Field of Search ................ 250/363 S, 445 T, 505, 250/511, 513

[56] References Cited

U.S. PATENT DOCUMENTS

| 3,790,782 | 2/1974 | Inoue et al. | 250/511 |
| 4,101,768 | 7/1978 | Lill | 250/445 T |
| 4,150,292 | 4/1979 | Ter-Pogossian | 250/363 S |
| 4,181,839 | 1/1980 | Hatton et al. | 250/363 S |

Primary Examiner—Alfred E. Smith
Assistant Examiner—Janice A. Howell
Attorney, Agent, or Firm—Fidelman, Wolffe & Waldron

[57] ABSTRACT

Emission computed tomograph wherein a plurality of detectors surround an object to be examined so as to detect X- or gamma radiation emitted by said object. In front of each of said detectors there is provided a collimator which comprises a pair of main plates and a subsidiary plate interposed therebetween. The plates are made of a material capable of blocking penetration of the radiation therethrough and so supported as to be swingable over an angle sufficient to cover the whole of said object. The plates of all the collimators are simultaneously swung to the same side and at the same angular speed thereby to change the direction of incidence of said radiation on each of said detectors.

9 Claims, 5 Drawing Figures

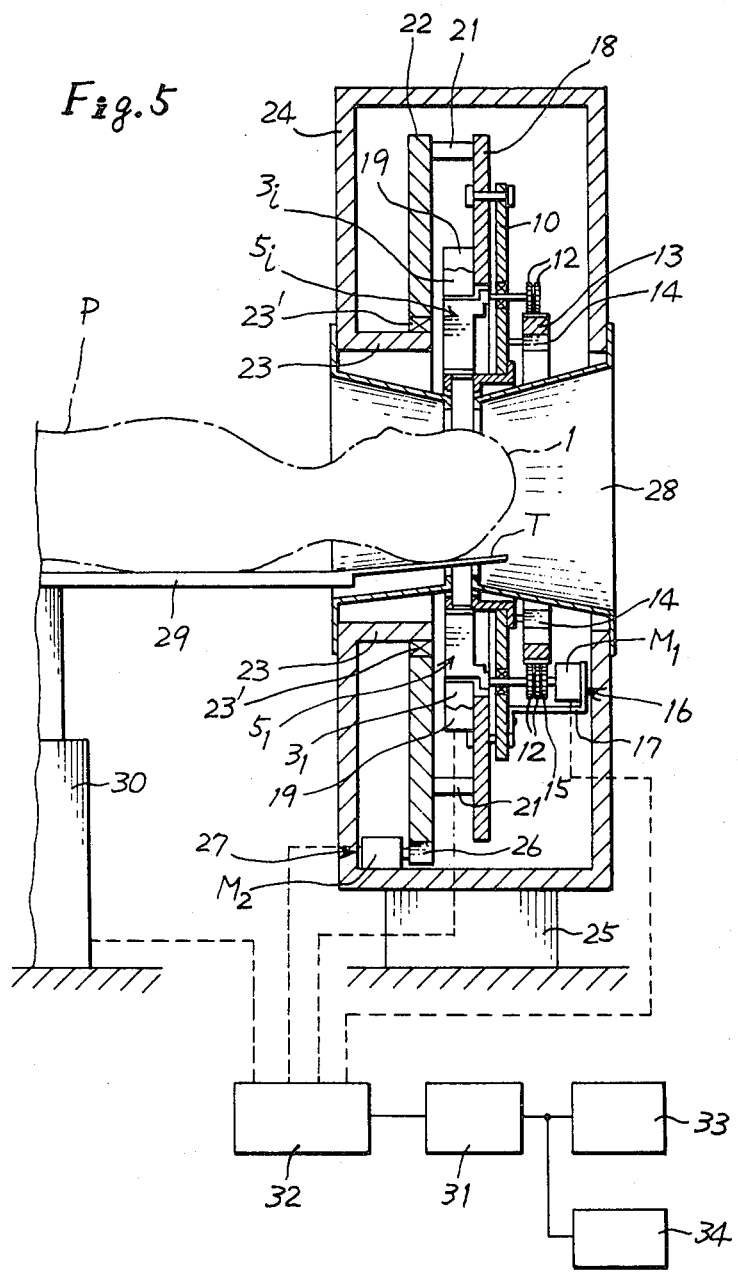

EMISSION COMPUTED TOMOGRAPH

BACKGROUND OF THE INVENTION

This invention relates to an emission computed tomograph.

Emission computed tomography commonly referred to as ECT is a technique for obtaining an image of the distribution of radioactivity of radioisotope within a desired plane perpendicular to the axis of the body of a patient being examined by administering to the patient a pharmaceutical compound labelled with the radioisotope, detecting from outside the body the radiation such as X-rays or gamma ($\gamma$) radiation emitted by the isotope that has been accumulated in a region or organ of the patient's body, and processing the detected data by an electronic computer.

In one known type of emission computed tomograph, scanning is conducted by rotating one or two Anger type detectors about the patient to be examined. In another type, the detector is adapted to traverse linearly across the patient, each tranverse being shifted a small angle from the previous one so as to cover the 360° region about the patient. With these arrangements, however, it is difficult to shorten the time required for obtaining all necessary data for reconstructing a tomographic image of the organ being examined.

Accordingly, the primary object of the invention is to provide an emission computed tomograph which is simple in construction with a relatively small number of movable component parts and therefore is reliable in operation.

Another object of the invention is to provide such an emission computed tomograph as aforesaid which requires a shorter time for measurement than the conventional devices.

The invention will be described in detail with reference to the accompanying drawing.

BRIEF DESCRIPTION OF THE DRAWING

FIG. 5 is a somewhat schematic elevational view, in vertical section, of the apparatus of the invention.

SUMMARY OF THE INVENTION

In accordance with the invention, a plurality of detectors surround a portion of the body of a patient to be examined so as to detect X- or $\gamma$-radiation emitted by the radioisotope that has been taken in by the patient and accumulated in the portion of the patient's body. In front of each of the detectors there is provided a collimator which comprises a pair of main plates and preferably a subsidiary plate interposed therebetween. The plates are made of a material capable of blocking penetration of the radiation therethrough and so supported as to be swingable over an angle sufficient to cover the whole of the portion of the patient's body. The plates of all the collimators are simultaneously swung in the same direction and at the same angular speed thereby to change the direction of incidence of the radiation on each of the detectors. The data collected by the detectors are processed by an electronic computer to reconstruct tomographic images of the portion of the patient's body being examined.

DESCRIPTION OF PREFERRED EMBODIMENTS

Figure 1:
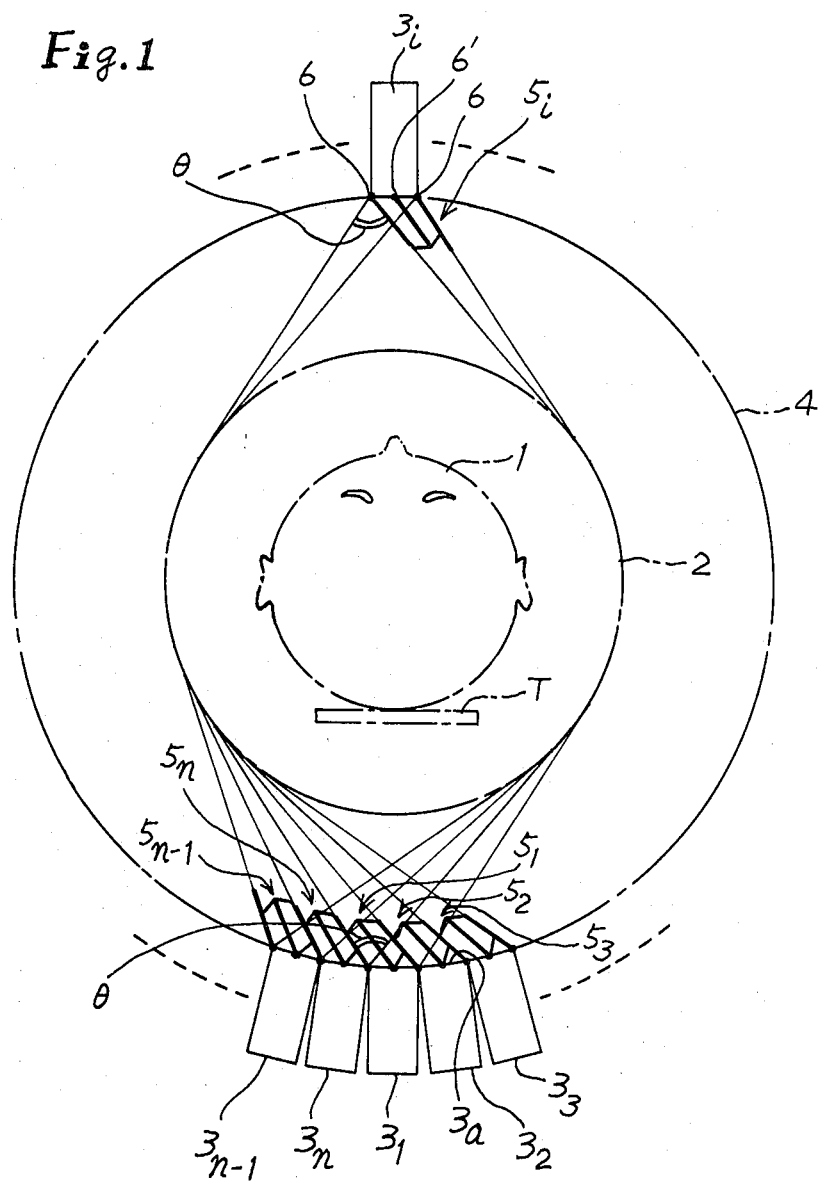
FIG. 1 schematically shows the principle of the invention.

Referring to FIG. 1, a part of a human body, e.g. the head 1 to be examined is shown supported by a suitable holder or table T in an area 2, within which it is possible to reconstruct tomographic images of the object being examined.

A plurality of gamma radiation detectors $3_1, 3_2, \ldots 3_i, \ldots 3_n$ are circumferentially arranged side by side and radially directed with their planes $3_a$ on which the radiation is incident being arranged along a circle 4 concentric with the circle defining the area 2.

A plurality of collimators $5_1, 5_2, \ldots 5_i, \ldots 5_n$ are provided in front of the detectors $3_1, 3_2, \ldots 3_i, \ldots 3_n$ for regulating the direction of the gamma radiation incident thereon. Each of the collimators comprises a pair of thin main plates $5a$ and $5b$ made of a material such as tungsten which is capable of blocking penetration of X- or gamma radiation therethrough. Each of the main plates $5a$ and $5b$ is pivotally supported at a point 6 on the circle 4 between each adjacent two of the detectors so that the plates $5a$ and $5b$ are swingable through an angle $\theta$ subtended by the two straight lines extending from each of the points 6 and being tangential to the circle defining the area 2. The angle $\theta$ is sufficient to cover the whole of the object to be examined. The plates $5a$ and $5b$ of all the collimators $5_1, 5_2, \ldots 5_i, \ldots 5_n$ are swung simultaneously and at the same angular speed by a suitable drive to be described presently.

Between the pair of main plates $5a$ and $5b$ there is interposed a thin subsidiary plate $5c$ made of a material similar to that of the main plates. The subsidiary plate $5c$ is pivoted at a point $6'$ intermediate the points 6 on the circle 4. A pair of spacer fins $7a$ and $7b$ are fixed to the opposite surfaces of the subidiary plate $5c$ intermediate the width or height thereof and projecting laterally outwardly perpendicularly thereto. Each of the fins $7a$ and $7b$ is positioned in the space between the subsidiary plate $5c$ and each of the main plates $5a$ and $5b$ so as to help position the subsidiary plate $5c$ substantially intermediate the main plates $5a$ and $5b$.

Strictly speaking, the width of each of the fins $7a$ and $7b$ is restricted by the size or width of the space between the main plates $5a$ and $5b$ when they are slanted or swung to the maximum angle. Therefore, under the condition that the main plates $5a$ and $5b$ are slanted to the maximum degree, the subsidiary plate $5c$ divides the space between the two main plates $5a$ and $5b$ in half. However, when the plates are directed radially toward the center of the circle 2 or 4, the subsidiary plate $5c$ does not exactly divide the space in half.

To keep the main and subsidiary plates at the same swing angle, one of the main plates and the subsidiary plate may be connected by extension bars and a connecting rod which form a parallelogram for simultaneous swinging of the plates.

FIGS. 2 to 5 somewhat schematically show a concrete structural arrangement of the apparatus of the invention, with the same reference numerals as in FIG. 1 designating corresponding parts.

Each of the main plates 5a and 5b of the collimators is formed with a boss 8 to which one end of a shaft 9 is fixed. The subsidiary plate 5c is also formed with a boss 8' to which one end of a shaft 9' is fixed. An annular plate 10 supports the shafts 9 and 9' of the main and the subsidiary plates 5a, 5b and 5c of all the collimators by means of a series of bearings 11 (only a few of which are shown in FIG. 2) arranged circumferentially in the annular support plate 10, so that the main and the subsidiary plates are circumferentially arranged and radially directed on one axial side of the annular plate 10.

The shaft 9 of each of the main plates 5a and 5b passes through the annular plate 10 so as to project from the opposite axial side thereof with a gear 12 fixed to the opposite end of the shaft 9. The shaft 9' of the subsidiary plate 5c, however, is provided with no such gear but merely received in the bearing 11.

Figure 2:
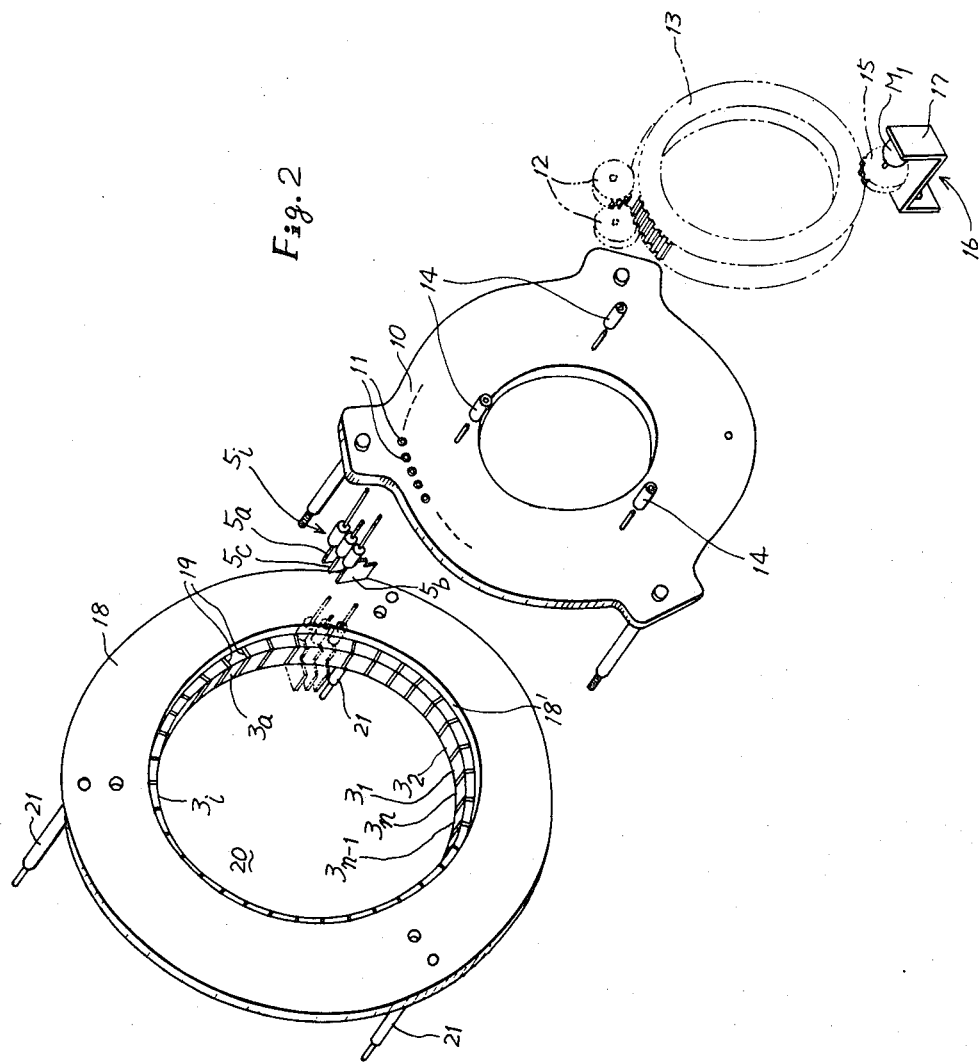
FIG. 2 is an exploded view of one embodiment of the invention, with some of the component parts being omitted for simplicity of illustration.
Figure 4:
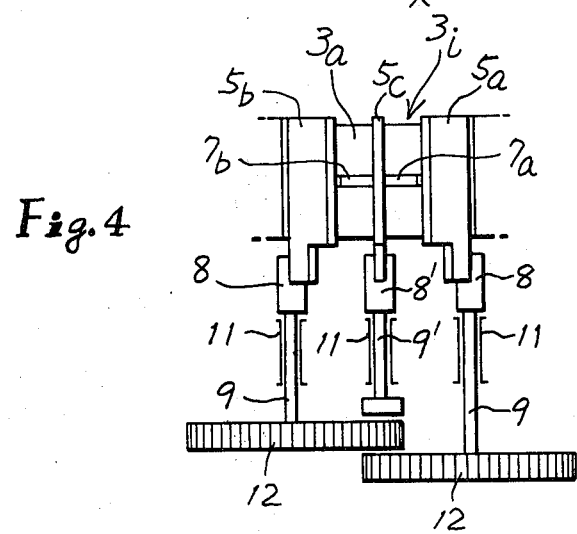
FIG. 4 is an elevational view of the collimator as viewed from below in FIG. 3.

The gears 12 thus fixed to the shafts 9 of the main plates of all the collimators $5_1, 5_2, \ldots 5_i, \ldots 5_n$ are circumferentially arranged on one axial side of the plate 10, although only two of the gears 12 are shown in FIG. 2 for simplicity of illustration. The gears 12 mesh with a large ring gear 13 which is rotatably mounted on the plate 10 by means of three rollers 14. The gears 12 are alternately displaced axially by a distance corresponding substantially to the thickness of the gear 12, as shown in FIG. 4, so that all the gears 12 can be arranged circumferentially about the ring gear 13 and mesh therewith.

A drive pinion 15 also meshes with the ring gear 13 and is rotated by a suitable driving device 16 which includes a reversible motor M1 and is fixed to the support plate 10 by a bracket 17. The pinion 15 is displaced axially from the gears 12 to enable meshing of the drive pinion 15 with the ring gear 13. As can be understood from the above description, the ring gear 13 has an axial thickness corresponding to at least the sum of double the axial thickness of the gear 12 and the axial thickness of the pinion 15.

It will be easily seen that upon rotation of the motor M1 in either direction the main and subsidiary plates 5a, 5b and 5c of all the collimators $5_1, 5_2, \ldots 5_i, \ldots 5_n$ are simultaneously swung in the same direction at the same angular speed.

An annular support plate 18 is provided on one axial end surface thereof with a plurality of radial ribs 19 axially projecting from the surface of the support plate 18. The ribs 19 are circumferentially spaced apart to define between each adjacent two ribs a space 19' in which one of the detectors $3_1, 3_2, \ldots 3_i, \ldots 3_n$ is fitted, so that the detectors are radially directed and circumferentially arranged side by side, with their planes 3a on which the radiation is incident facing radially inwardly to define a circular aperture 20 concentric with the central aperture 18' of the annular support plate 18.

The two support plate 10 and 18 are axially put together so that the collimators $5_1, 5_2, \ldots 5_i, \ldots 5_n$ are arranged radially inwardly in front of the corresponding detectors $3_1, 3_2, \ldots 3_i, \ldots 3_n$ as shown in FIG. 1.

The plate 18 is connected by studs 21 to an annular support plate 22 which is in turn mounted by means of a bearing 23' on a flange 23 formed in a gantry 24 which encloses the above-mentioned and other component parts of the apparatus. A base 25 supports the gantry 24.

A roller 26 frictionally contacts the peripheral surface of the annular support plate 22 and is rotated by a driving device 27 including a reversible motor M2 thereby to change the circumferential position of the support plate 22 and all the parts mounted thereon or connected thereto.

The gantry 24 has a central tunnel 28 in which the head holder T can be placed. The head holder is attached to a bed 29 which is slidably supported on a base 30.

Figure 3:
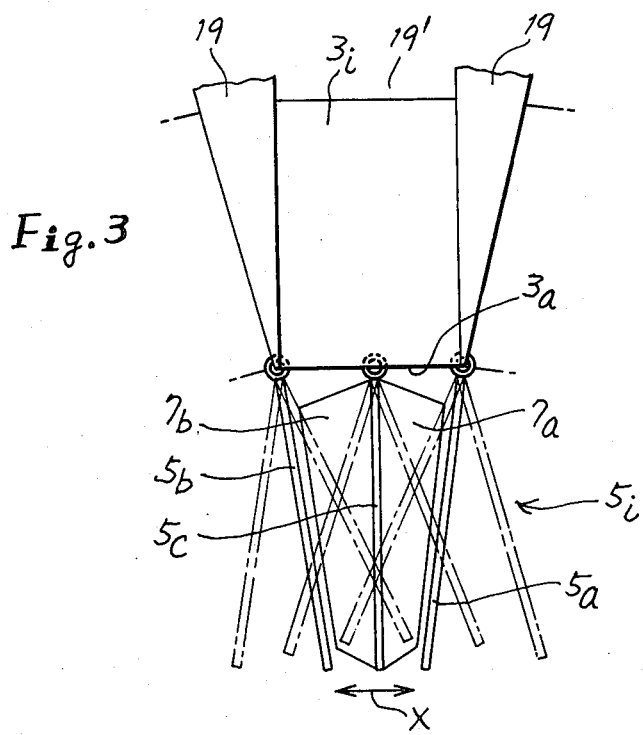
FIG. 3 is a somewhat schematic enlarged top plan view of the collimator constructed in accordance with the invention.

In operation, the gamma radiation emerging from the head 1 of a patient P being examined passes through the spaces between the subsidiary plate 5c and the adjacent main plates 5a and 5b of the collimators to enter the detectors behind them, with resulting improvement in collimation in the circumferential direction shown by the arrow X in FIG. 3.

As the main plates 5a and 5b are swung to either side by rotating the motor M1, the movement of the main plate 5a or 5b is transferred through the spacer fin 7a or 7b or otherwise to the subsidiary plate 5c to swing it to the same side substantially synchronously with the main plates 5a and 5b. This enables one and the same detector to detect the radiation coming in various directions from the head 1 being examined, thereby to obtain in a short time sufficient data to reconstruct a tomographic image of head 1.

The motor M1 is controlled by a computer 31 through an interface 32 and the data collected by the detectors are processed in the computer 31 so as to reconstruct a tomographic image of the head 1, which is displayed on a suitable display unit 33 or recorded by a recorder 34 such as a magnetic disk.

Having illustrated one preferred embodiment of the invention, there may be many changes and modifications thereof. For example, the spacer fins 7a and 7b may be attached to the main plates 5a and 5b instead of the subsidiary plate 5c. Although in the illustrated embodiment a single spacer fin is provided in the space between the subsidiary plate and each of the main plates, there may be provided a plurality of such spacer fins in the space. A plurality of subsidiary plates may be provided between the main plates 5a and 5b. The subsidiary plate 5c with the spacer fins 7a and 7b may be ommited if the resulting degradation of collimation is tolerable.

As described above in detail, with the apparatus of the invention it is possible to shorten the time required for measurment. Since the radiation entering adjacent detectors is separated only by a single thin plate, the mechanical thickness of which can be reduced to the minimum required for blocking the radiation, the detector can have a large aperture through which the incident radiation enters the detector, with resulting increase in the sensitivity. Since the collimators comprise thin plates, the structure is simple and easy to manufacture and low in cost. Since the detectors are mechanically fixed, reliability is increased. The subsidiary plate 5c, if interposed between the main plates of the collimator so as to be moved by the main plates, improves collimation in the circumferential direction, and with the spacer fins 7a and 7b added collimation can be improved in the direction of thickness of the tomographic slice.

What we claim is:

1. An emission computed tomograph comprising: means for supporting an object to be examined at a predetermined position, said object having taken therein a radionuclide that emits penetrating radiation such as X- or gamma radiation; a plurality of radiation detectors; means for supporting said detectors side by side along a circle about said predetermined position so that the radiation incident planes of said detectors face said object so as to receive radiation from said objects the position of each of said detectors being stationary relative to said object; a plurality of collimators; means for supporting said collimators between said predetermined position and said detectors so that each of said collimators is disposed in front of one of said detectors; each of said collimators comprising a pair of thin main plates made of a material capable of blocking penetration of said radiation therethrough, said main plates extending radially inwardly of said circle so as to define the direction in which said radiation from said object is incident on said radiation incident plane of said detector, and said main plates having an axis of rotation at a border between said radiation incident planes of each adjacent two of said detectors so that said main plates are swingable about said respective axes over a predetermined angle sufficient to cover the whole of said object; and means for causing said main plates of all said collimators to synchronously swing in the same direction and at the same angular speed thereby to scan the whole of the area in which the tomographic image of said object is to be reconstructed.

2. The apparatus of claim 1, wherein each of said main plates of said collimators has a shaft for rotation about said axis; said collimator supporting means comprises an annular plate provided with a plurality of bearings circumferentially arranged, each of which receives one of said shafts of said main plates of all said collimators; and said causing means comprises a plurality of gears of the same size, each of which is fixed to one of said shafts of said main plates of all said collimators, a single ring gear meshing with said plurality of gears simultaneously, and means for rotating said ring gear in either direction thereby to rotate said plurality of gears and consequently swing said main plates of all said collimators simultaneously in the same direction and at the same angular speed.

3. The apparatus of claim 1, wherein each of said collimators further includes at least one subsidiary plate having substantially the same structure as said main plates and interposed therebetween.

4. The apparatus of claim 3, wherein each of said collimators further includes at least one spacer fin interposed between said subsidiary plate and each of said main plates.

5. The apparatus of claim 4, wherein said spacer fins are attached to the opposite sides of said subsidiary plate.

6. The apparatus of claim 4, wherein one of said spacer fins is attached to one of said main plates while the other of said spacer fins is attached to the other of said main plates.

7. The apparatus of claim 4, wherein said spacer fins are made of a material capable of blocking penetration of said radiation therethrough.

8. The apparatus of claim 4, wherein each of said main and subsidiary plates of said collimators has a shaft mounted for rotation about said axis; and said collimator supporting means comprises an annular plate provided with a plurality of bearings circumferentially arranged, each of said bearings receiving one of said shafts; and said causing means comprises a plurality of gears of the same size, each of which is fixed to one of said shafts of said main plates, a single ring gear meshing with said plurality of gears simultaneously, and means for rotating said ring gear in either direction thereby to rotate said plurality of gears and consequently swing said main and subsidiary plates of all said collimators simultaneously in the same direction and at the same angular speed.

9. The apparatus of claim 3, wherein one of said main plates and said subsidiary plate of each of said collimators are mechanically connected for simultaneous swinging in the same direction at the same angular speed.

* * * * *